(12) United States Patent
Nakamura et al.

(10) Patent No.: US 12,215,182 B2
(45) Date of Patent: Feb. 4, 2025

(54) URETHANE PREPOLYMER, ADHESIVE, SKIN PATCH MATERIAL, ADHESIVE TAPE, WEARABLE DEVICE, AND WEARABLE DEVICE KIT

(71) Applicant: AGC Inc., Tokyo (JP)

(72) Inventors: Makito Nakamura, Tokyo (JP); Haru Kawasaki, Tokyo (JP); Hitoshi Shimoma, Tokyo (JP); Chitoshi Suzuki, Tokyo (JP); Hiroshi Wada, Tokyo (JP)

(73) Assignee: AGC Inc., Tokyo (JP)

( * ) Notice: Subject to any disclaimer, the term of this patent is extended or adjusted under 35 U.S.C. 154(b) by 647 days.

(21) Appl. No.: 17/399,512

(22) Filed: Aug. 11, 2021

(65) Prior Publication Data

US 2021/0371574 A1 Dec. 2, 2021

Related U.S. Application Data

(63) Continuation of application No. PCT/JP2020/006116, filed on Feb. 17, 2020.

(30) Foreign Application Priority Data

Feb. 28, 2019 (JP) .................. 2019-036306

(51) Int. Cl.

| | | |
|---|---|---|
| *C09J 175/08* | (2006.01) | |
| *A61B 5/00* | (2006.01) | |
| *C08G 18/12* | (2006.01) | |
| *C08G 18/48* | (2006.01) | |
| *C09J 7/38* | (2018.01) | |

(52) U.S. Cl.
CPC ............ *C08G 18/12* (2013.01); *A61B 5/6833* (2013.01); *C08G 18/4833* (2013.01); *C09J 7/38* (2018.01); *C09J 175/08* (2013.01); *C08G 2170/40* (2013.01)

(58) Field of Classification Search
CPC .... C08G 18/12; C08G 18/4833; C09J 175/08; C09J 7/38
See application file for complete search history.

(56) References Cited

U.S. PATENT DOCUMENTS

| | | | |
|---|---|---|---|
| 5,045,601 A | | 9/1991 | Capelli et al. |
| 5,591,820 A | * | 1/1997 | Kydonieus ............ A61L 31/148 |
| | | | 528/905 |
| 6,531,566 B1 | * | 3/2003 | Satake ............... C08G 18/6674 |
| | | | 528/424 |

FOREIGN PATENT DOCUMENTS

| | | |
|---|---|---|
| EP | 0 597 636 A1 | 5/1994 |
| JP | 5457446 B2 | 4/2014 |
| JP | 2019-21 4655 A | 12/2019 |

OTHER PUBLICATIONS

International Search Report issued Apr. 21, 2020 in PCT/JP2020/006116, filed on Feb. 17, 2020, 2 pages.

* cited by examiner

*Primary Examiner* — Michael L Leonard
(74) *Attorney, Agent, or Firm* — Oblon, McClelland, Maier & Neustadt, L.L.P.

(57) ABSTRACT

Provided are a urethane prepolymer from which is obtained an adhesive which has excellent moisture permeability and which attains both low adhesion to skin and high adhesion to a base material, an adhesive, a skin patch material, an adhesive tape, a wearable device, and a wearable device kit. The urethane prepolymer is a hydroxyl-group-terminated urethane prepolymer obtained by reacting an oxyalkylene polymer A having an average number of hydroxyl groups per molecule of 2.1 to 3, an oxyalkylene polymer B in which the number of hydroxyl groups per molecule is 1, and a diisocyanate compound, the number-average molecular weight of the oxyalkylene polymer B being 5000 or greater, and the content of ethylene oxide units in the hydroxyl-group-terminated urethane prepolymer being more than 10 mass %.

23 Claims, No Drawings

URETHANE PREPOLYMER, ADHESIVE, SKIN PATCH MATERIAL, ADHESIVE TAPE, WEARABLE DEVICE, AND WEARABLE DEVICE KIT

TECHNICAL FIELD

The present invention relates to a polyurethane prepolymer, an adhesive, an adhesive skin patch, an adhesive tape, a wearable device and a wearable device kit.

BACKGROUND ART

Pressure-sensitive adhesives to be applied to skin are required to have excellent moisture permeability so that when used as a pressure-sensitive adhesive layer of an adhesive skin patch, moisture due to sweating from the skin would evaporate to outside of the adhesive skin patch.

Patent Document 1 discloses an adhesive which is a polyurethane type adhesive for skin having moisture permeability of at least 5,000 g/m²·day and which is obtained by reacting (1) a polyol having a number average molecular weight of at least 5,000 and an average number of functional groups of at least 2 and having a polyoxyalkylene structure, (2) a polyol having a number average molecular weight of from 1,500 to 5,000 and an average number of functional groups of 1 and having a polyoxyalkylene structure, and (3) an organic polyisocyanate. The average number of functional groups in all the polyols used for obtaining the above adhesive is from 2 to 2.6, and the content of ethylene oxide units in all the polyols in the above adhesive is from 3 to 8 wt %.

Further, in recent years, an adhesive for attaching a wearable device to the skin is starting to be used, and such an adhesive is required to have a low adhesion to the skin so that the skin would not be damaged when removing the wearable device from the skin, while required to have a high adhesion to the wearable device body.

PRIOR ART DOCUMENTS

Patent Document

Patent Document 1: Japanese Patent No. 5457446

DISCLOSURE OF INVENTION

Technical Problem

Pressure-sensitive adhesives to be applied to the skin are required to have excellent moisture permeability and also have both a low adhesion to the skin and a high adhesion to a substrate.

However, the adhesive disclosed in Patent Document 1 has a high adhesion to both the skin and a substrate, and if applied to the skin, the skin may be damaged when removing the adhesive from the skin.

Under these circumstances, it is an object of the present invention to provide a polyurethane prepolymer whereby an adhesive having excellent moisture permeability and also having both a low adhesion to the skin and a high adhesion to a substrate can be obtained, an adhesive, an adhesive skin patch, an adhesive tape, a wearable device and a wearable device kit.

Solution to Problem

The above object is achieved by the following constructions.

[1] A hydroxy group-terminated polyurethane prepolymer which is obtained by reacting an oxyalkylene polymer A having an average number of hydroxy groups per molecule of from 2.1 to 3, an oxyalkylene polymer B having one hydroxy group per molecule, and a diisocyanate compound, wherein
  the number average molecular weight of the oxyalkylene polymer B is at least 5,000, and
  the content of ethylene oxide units in the hydroxy group-terminated polyurethane prepolymer is more than 10 mass %.

[2] The hydroxy group-terminated polyurethane prepolymer according to the above [1], wherein the number average molecular weight of the oxyalkylene polymer B is more than 5,000.

[3] The hydroxy group-terminated polyurethane prepolymer according to the above [1] or [2], wherein the oxyalkylene polymer A contains
  an oxyalkylene polymer a having three hydroxy groups per molecule and
  an oxyalkylene polymer b having two hydroxy groups per molecule.

[4] The hydroxy group-terminated polyurethane prepolymer according to the above [3], wherein the content of ethylene oxide units in the oxyalkylene polymer a is at least 15 mass %.

[5] The hydroxy group-terminated polyurethane prepolymer according to any one of the above [1] to [4] which has an average number of hydroxy groups of less than 3.0.

[6] The hydroxy group-terminated polyurethane prepolymer according to any one of the above [1] to [5], wherein the content of ethylene oxide units in the hydroxy group-terminated polyurethane prepolymer is from 12 to 50 mass %.

[7] A pressure-sensitive adhesive which is obtained by reacting the hydroxy group-terminated polyurethane prepolymer as defined in any one of the above [1] to [6] and a curing agent containing a polyisocyanate compound having at least three isocyanate groups in one molecule, wherein the content of ethylene oxide units in the adhesive is at least 10 mass %.

[8] A pressure-sensitive adhesive which is obtained by reacting an oxyalkylene polymer A having an average number of hydroxy groups per molecule of from 2.1 to 3, an oxyalkylene polymer B having one hydroxy group per molecule, and a polyisocyanate compound, wherein the number average molecular weight of the oxyalkylene polymer B is at least 5,000, and the content of ethylene oxide units in the adhesive is at least 10 mass %.

[9] The pressure-sensitive adhesive according to the above [8], wherein the number average molecular weight of the oxyalkylene polymer B is more than 5,000.

[10] The pressure-sensitive adhesive according to the above [8] or [9], wherein the oxyalkylene polymer A contains
  an oxyalkylene polymer a having three hydroxy groups per molecule and
  an oxyalkylene polymer b having two hydroxy groups per molecule.

[11] The pressure-sensitive adhesive according to the above [10], wherein the content of ethylene oxide units in the oxyalkylene polymer a is at least 15 mass %.

[12] The pressure-sensitive adhesive according to any one of the above [8] to [11], wherein the content of ethylene oxide units in the adhesive is from 12 to 50 mass %.

[13] The pressure-sensitive adhesive according to any one of the above [8] to [12], which has a storage elastic modulus at 80° C. of at most $4.0 \times 10^5$ Pa.

[14] The pressure-sensitive adhesive according to any one of the above [8] to [13], which has a moisture permeability of at least 3,000 g/m²·day.
[15] The pressure-sensitive adhesive according to any one of the above [8] to [14], which has an adhesion to human skin, of from 0.2 to 1 N/15 mm.
[16] The pressure-sensitive adhesive according to any one of the above [8] to [15], wherein the difference between adhesion to a phenol resin and adhesion to human skin is at least 2 N/15 mm.
[17] An adhesive skin patch comprising a substrate and a pressure-sensitive adhesive layer containing the pressure-sensitive adhesive as defined in any one of the above [8] to [16], formed on a surface of the substrate.
[18] A pressure-sensitive adhesive tape comprising a substrate and a pressure-sensitive adhesive layer containing the adhesive as defined in any one of the above [8] to [16], formed on at least one surface of the substrate.
[19] A wearable device comprising a wearable device body and a pressure-sensitive adhesive layer containing the pressure-sensitive adhesive as defined in any one of the above [8] to [16], formed on at least a part of an adherend surface of the wearable device body.
[20] A wearable device kit comprising a wearable device body and the pressure-sensitive adhesive as defined in any one of the above [8] to [16], the adhesive skin patch as defined in the above [17] or the pressure-sensitive adhesive tape as defined in the above [18], for attaching the wearable device body to skin.

Advantageous Effects of Invention

According to the present invention, it is possible to provide a polyurethane prepolymer whereby an adhesive having excellent moisture permeability and also having both low adhesion to the skin and high adhesion to a substrate can be obtained, an adhesive, an adhesive skin patch, an adhesive tape, a wearable device and a wearable device kit.

DESCRIPTION OF EMBODIMENTS

In this specification, definitions and meanings of terms are as follows.

"Oxyalkylene polymer" is a polymer having a polyoxyalkylene chain. Further, repeating units based on an alkylene oxide are referred to as "alkylene oxide units".

"Hydroxy group-terminated polyurethane prepolymer" is a compound having a hydroxy group at least at a part of terminals of the molecular chain and a urethane bond in the molecular chain, which is obtained by reacting an organic compound having a hydroxy group and a diisocyanate compound. Further, in this specification, "isocyanate group-terminated polyurethane prepolymer" is a compound having an isocyanate group at least at a part of terminals of the molecular chain and a urethane bond in the molecular chain, which is obtained by reacting an organic compound having at least 2 hydroxy groups in one molecule and a polyisocyanate compound.

The number average molecular weight (hereinafter referred to also as "Mn") and the molecular weight distribution (hereinafter referred to also as "Mw/Mn") of the oxyalkylene polymer are values measured by the methods described below.

As standard samples for molecular weight measurement, the molecular weight of several types of monodispersed polypropylene glycol polymers having different degrees of polymerization is measured by means of a commercially available GPC measuring apparatus (HLC-8320GPC, manufactured by Tosoh Corporation), a calibration curve is prepared based on the relation between the molecular weight of the polypropylene glycol and the retention time, an oxyalkylene polymer as a measurement sample is diluted to 0.5 mass % with tetrahydrofuran and filtered through a 0.5 μm filter, and then the molecular weight of the measurement sample is measured by means of the GPC measuring apparatus. Mn and the mass average molecular weight (hereinafter referred to also as Mw) of the measurement sample are obtained by analyzing the GPC spectrum of the sample to be measured by a computer.

The molecular weight distribution is a value obtained by dividing Mw by Mn.

The degree of unsaturation of the oxyalkylene polymer is a value measured in accordance with the method stipulated in JIS K1557-6.

The hydroxy value of the oxyalkylene polymer is a value measured and calculated in accordance with the titration method stipulated in JIS K0070: 1992 "Test methods for acid value, saponification value, ester value, iodine value, hydroxyl value and unsaponifiable matter of chemical products".

[Hydroxy Group-Terminated Polyurethane Prepolymer]

The hydroxy group-terminated polyurethane prepolymer of the present invention is one obtained by reacting an oxyalkylene polymer A, an oxyalkylene polymer B and a diisocyanate compound. Hydroxy groups in the oxyalkylene polymer A and the oxyalkylene polymer B react with isocyanate groups in the diisocyanate compound, whereby urethane bonds between the diisocyanate compound, and the oxyalkylene polymer A and the oxyalkylene polymer B are formed. Among the hydroxy groups in the oxyalkylene polymer A and the oxyalkylene polymer B, hydroxy groups remaining unreacted with the isocyanate groups in the diisocyanate compound will be hydroxy groups at the terminal of the molecular chain of the polyurethane prepolymer.

<Oxyalkylene Polymer A>

The oxyalkylene polymer A (hereinafter referred to also as polymer A) is an oxyalkylene polymer having an average number of hydroxy groups per molecule of from 2.1 to 3.

The average number of hydroxy groups per molecule of the oxyalkylene polymer A is not particularly limited, so long as it is from 2.1 to 3, and is preferably from 2.2 to 2.8. When the average number of hydroxy groups falls within the above range, the moisture permeability will be more excellent, and both a low adhesion to the skin and a high adhesion to a substrate will be easily established.

When the average number of hydroxy groups of the oxyalkylene polymer A falls within the range of from 2.1 to 3, a pressure-sensitive adhesive to be obtained tends to have appropriate adhesion to the skin and adhesion to a substrate, and adhesive residue when released from the skin will be little. Here, adhesive residue means that the adhesive remains on the skin when the pressure-sensitive adhesive is attached to the skin and removed.

The average number of hydroxy groups per molecule of the oxyalkylene polymer A is a value calculated by specifying the type and the molar ratio of an initiator by $^{13}$C-NMR (nuclear magnetic resonance). In the $^{13}$C-NMR analysis, peaks characteristic of the initiator are observed, and the type and the molar ratio of the initiator can be identified from the positions of the peaks and the peak areas.

The number of hydroxy groups per molecule of the oxyalkylene polymer usually corresponds to the number of hydroxy groups per molecule of the initiator used for preparing the oxyalkylene polymer. For example, when glycerin is used as the initiator for preparing an oxyalkylene polymer, an oxyalkylene polymer having three hydroxy groups per molecule is usually obtained. Further, for example, when pentaerythritol is used as the initiator for preparing an oxyalkylene polymer, an oxyalkylene polymer having four hydroxy groups per molecule is usually obtained. Further, for example, when dipropylene glycol is used as the initiator for preparing an oxyalkylene polymer, an oxyalkylene polymer having two hydroxy groups per molecular is usually obtained.

The average number of hydroxy groups per molecule of the oxyalkylene polymer A is a value calculated from the number of hydroxy groups per molecule based on the type of the initiator and the molar fraction of the initiator. For example, when glycerin is 30 mol %, and dipropylene glycol is 70 mol %, the average number of hydroxy groups is $3 \times 0.3 + 2 \times 0.7 = 2.3$.

The alkylene oxide used for preparing the oxyalkylene polymer A is not particularly limited, and is preferably a $C_{2-5}$ alkylene oxide, more preferably at least one type selected from ethylene oxide and propylene oxide, further preferably propylene oxide alone or a combination of ethylene oxide and propylene oxide.

In the case of the combination of propylene oxide and ethylene oxide, the arrangement of ethylene oxide units and propylene oxide units may be random or block.

In a case where as the alkylene oxide, a combination of ethylene oxide and an alkylene oxide other than ethylene oxide is used, the molar ratio of ethylene oxide and the alkylene oxide other than ethylene oxide is not particularly limited, and the molar ratio is preferably such that the content of ethylene oxide units in the oxyalkylene polymer A would fall within the after-mentioned range. The higher the content of ethylene oxide units is, the more the hydrophilicity of the oxyalkylene polymer A improves, and the lower the content of ethylene oxide units is, the more the crystallinity of the oxyalkylene polymer A tends to decrease.

The content of ethylene oxide units in the oxyalkylene polymer A is not particularly limited, and is preferably from 0 to 80 mass %, more preferably from 0 to 60 mass %, further preferably from 5 to 55 mass %, still more preferably from 12 to 50 mass %. When the content of ethylene oxide units in the oxyalkylene polymer A falls within the above range, the oxyalkylene polymer A tends to be non-crystalline, whereby the handling efficiency will be good, and a pressure-sensitive adhesive to be obtained will have an appropriate adhesion to the skin.

The content of ethylene oxide units in the oxyalkylene polymer A is a value calculated from the monomer composition of the oxyalkylene chain obtained by $^{13}$C-NMR. For example, in a case where the oxyalkylene polymer A is a polyol comprising propylene oxide units and ethylene oxide units, the content of ethylene oxide units can be obtained from the area ratio of signal of methyl groups in the propylene oxide units and signal of methylene groups in the propylene oxide units and the ethylene oxide units.

Mn of the oxyalkylene polymer A is not particularly limited, and is preferably from 1,000 to 50,000, more preferably from 5,000 to 30,000. When Mn of the oxyalkylene polymer A falls within the above range, a pressure-sensitive adhesive to be obtained will have better flexibility. Further, a pressure-sensitive adhesive to be obtained will have more appropriate adhesion and adhesive residue.

In a case where two or more types of oxyalkylene polymer A are contained, it is preferred that Mn, Mw/Mn, the degree of unsaturation and the average number of functional groups of the respective oxyalkylene polymers A fall within the above ranges.

The oxyalkylene polymer A preferably contains an oxyalkylene polymer a (hereinafter referred to also as "polymer a") having three hydroxy groups per molecule and an oxyalkylene polymer b (hereinafter referred to also as "polymer b") having two hydroxy groups per molecule. When the oxyalkylene polymer A contains both the polymer a and the polymer b, the adhesion to the skin and the adhesion to a substrate tend to fall within more appropriate ranges.

The polymer a may be two or more types.

The content of ethylene oxide units in the polymer a is not particularly limited and is preferably at least 0 mass %, more preferably from 10 to 80 mass %, further preferably from 15 to 60 mass %, still more preferably from 15 to 30 mass %. When two or more types of polymer a are contained, the content of ethylene oxide units as a value calculated by weighted average of them preferably falls within the above range.

Further, Mn of the polymer a is not particularly limited and is preferably from 1,000 to 50,000, more preferably from 5,000 to 30,000, further preferably from 8,000 to 25,000. When two or more polymers a are contained, Mn of the respective polymers a preferably falls within the above range.

Mw/Mn of the polymer a is not particularly limited and is preferably less than 1.20, more preferably less than 1.13, particularly preferably less than 1.10. When the molecular weight distribution of the polymer a is made to be less than 1.20, the reactivity will be good, the after-mentioned polyurethane prepolymer can be efficiently produced, and the polyurethane prepolymer to be obtained tends to have a lower viscosity.

The degree of unsaturation of the polymer a is preferably at most 0.015 meq/g, more preferably at most 0.013 meq/g, further preferably at most 0.008 meq/g. The degree of unsaturation of the oxyalkylene polymer a may be 0. When the degree of unsaturation of the polymer a is at most the upper limit value, a prepolymer to be obtained will have more favorable curability, and adhesive residue to the skin will be further reduced.

When two or more types of oxyalkylene polymer a are contained, Mn, Mw/Mn and the degree of unsaturation of the respective polymers a preferably fall within the above ranges.

The polymer b may be two or more types.

The content of ethylene oxide units in the polymer b is not particularly limited and is preferably at least 0 mass %, more preferably from 10 to 80 mass %, further preferably from 15 to 60 mass %, still more preferably from 15 to 30 mass %. When two or more types of polymer b are contained, the content of ethylene oxide units as a value calculated by weighted average of them preferably falls within the above range.

Further, Mn of the oxyalkylene polymer b is not particularly limited and is preferably from 1,000 to 50,000, more preferably from 5,000 to 30,000, further preferably from 8,000 to 25,000. When two or more types of the polymer b are contained, Mn of the respective polymers b preferably fall within the above range.

Mw/Mn of the polymer b is not particularly limited and is preferably less than 1.20, further preferably less than 1.13, particularly preferably less than 1.10. When the molecular weight distribution of the oxyalkylene polymer b is less than 1.20, the reactivity will be good, the after-mentioned polyurethane prepolymer can be efficiently produced, and the polyurethane prepolymer to be obtained tends to have a lower viscosity.

The degree of unsaturation of the polymer b is preferably at most 0.015 meq/g, more preferably at most 0.013 meq/g, further preferably at most 0.008 meq/g. The degree of unsaturation of the oxyalkylene polymer b may be 0. When the degree of unsaturation of the polymer b is at most the upper limit value, a prepolymer to be obtained will have more favorable curability, and adhesive residue to the skin will be further reduced.

When two or more types of polymer b are contained, Mn, Mw/Mn and the degree of unsaturation of the respective polymers b preferably fall within the above ranges.

The content of the polymer a to the total mass of the polymer a and the polymer b is not particularly limited and is preferably from 5 to 95 mass %, more preferably from 10 to 80 mass %, further preferably from 15 to 60 mass %. When the content of the polymer a to the total mass of the polymer a and the polymer b falls within the above range, adhesive residue will be little when a pressure-sensitive adhesive to be obtained is removed from the skin.

The proportion of the polymer a and the polymer b contained in the oxyalkylene polymer A can be calculated as described below.

The hydroxy value of the oxyalkylene polymer A is calculated in accordance with the titration method in JIS K0070: 1992 "Test methods for acid value, saponification value, ester value, iodine value, hydroxyl value and unsaponifiable matter of chemical products". Further, the number average molecular weight of the oxyalkylene polymer A in terms of the oxyalkylene polymer is calculated by GPC measurement and by analysis by an analytical curve obtained using an oxyalkylene polymer as a standard substance.

The hydroxy value and Mn obtained as described above are applied to the formula of "(hydroxy value×Mn)/56,100" to calculate the average number of hydroxy groups.

Next, the type of the initiator contained in the oxyalkylene polymer A is identified by confirming e.g. the presence or the absence of a tertiary carbon atom derived from glycerin, and from the information of the average number of hydroxy groups and the type of the initiator, the content of units derived from each initiator is obtained to calculate the proportions of the polymer a and the polymer b contained in the oxyalkylene polymer A.

So long as the average number of hydroxy groups per molecule is from 2.1 to 3, the oxyalkylene polymer A may contain an oxyalkylene polymer other than the polymer a, the polymer b and the oxyalkylene polymer B. As such an oxyalkylene polymer other than the oxyalkylene polymer a, the oxyalkylene polymer b and the oxyalkylene polymer B, an oxyalkylene polymer having at least 4 hydroxy groups per molecule and an oxyalkylene polymer having Mn of less than 5,000 and one hydroxy group per molecule may be mentioned.

The proportion of the total mass of the polymer a and the polymer b in the oxyalkylene polymer A is preferably at least 80 mass %, more preferably at least 90 mass %, further preferably 100 mass %.

The method for producing the oxyalkylene polymer A is not particularly limited and may be a method of respectively preparing the polymer a having three hydroxy groups per molecule and the polymer b having two hydroxy groups per molecule and mixing them, or a method of producing an oxyalkylene polymer A as a mixture of the polymer a having three hydroxy groups per molecule and the polymer b having two hydroxy groups per molecule.

For preparing the oxyalkylene polymer A, it is preferred to subject an alkylene oxide to ring-opening addition to an initiator having at least two hydroxy groups in one molecule in the presence of a catalyst.

For preparing the polymer b, an initiator having two hydroxy groups in one molecule is used. As the initiator having two hydroxy groups in one molecule for preparing the polymer b, at least one member selected from the group consisting of ethylene glycol, diethylene glycol, propylene glycol and dipropylene glycol is preferred, at least one member selected from propylene glycol and dipropylene glycol is more preferred, and propylene glycol is further preferred. Propylene glycol is available at a low cost, whereby a cost for preparing the polymer b can be reduced.

An initiator having three hydroxy groups in one molecule is used for preparing the polymer a. As the initiator for preparing the polymer a, glycerin is preferred. Glycerin is available at a low cost, whereby the cost for preparing the oxyalkylene polymer a can be reduced.

An initiator having at least 4 hydroxy groups in one molecule is used for preparing an oxyalkylene polymer having at least 4 hydroxy groups per molecule which the oxyalkylene polymer A may contain. As the initiator having at least 4 hydroxy groups per molecule, a tetrahydric or higher polyhydric alcohol such as diglycerin, pentaerythritol, dipentaerythritol and tripentaerythritol, a saccharide such as glucose, sorbitol, dextrose, fructose, sucrose and methyl glycoside or derivatives thereof may be mentioned, but the initiator is by no means limited thereto.

An initiator having one hydroxy group in one molecule is used for preparing an oxyalkylene polymer having one hydroxy group per molecule which the oxyalkylene polymer A may contain. The initiator having one hydroxy group in one molecule is the same initiator to be used for preparing the after-mentioned oxyalkylene polymer B. However, the oxyalkylene polymer having one hydroxy group per molecule which may be contained in the oxyalkylene polymer A has Mn of less than 5,000.

Initiators having different numbers of hydroxy groups in one molecule are mixed and used for preparing the oxyalkylene polymer A as a mixture of oxyalkylene polymers having different numbers of hydroxy groups per molecule. The types and the amount of initiators used are controlled so that the oxyalkylene polymer to be obtained would have an average number of hydroxy groups of from 2.1 to 3.

An alkylene oxide used for preparing the polymer a, the polymer b, an oxyalkylene polymer having at least 4 hydroxy groups per molecule and an oxyalkylene polymer having Mn of less than 5,000 and one hydroxy group per molecule is the same as the alkylene oxide used for preparing the above mentioned oxyalkylene polymer A.

As a catalyst for ring-opening addition polymerization of the alkylene oxide to the initiator, known catalysts may be used. For example, an alkaline catalyst such as KOH, a transition metal compound-porphyrin complex catalyst such as a complex to be obtained by reacting an organic aluminum compound and a porphyrin, a double metal cyanide complex catalyst and a catalyst comprising a phosphazene compound may be mentioned.

When the oxyalkylene polymer A is obtained by using the double metal cyanide complex catalyst, the molecular weight distribution of the oxyalkylene polymer A to be obtained can be made narrow, and the oxyalkylene polymer A having a low viscosity tends to be obtained.

As the double metal cyanide complex, known compounds may be used, and known methods for producing a polymer with the double metal cyanide complex may be employed. For example, compounds and production methods disclosed in WO2003/062301, WO2004/067633, JP-A-2004-269776, JP-A-2005-015786, WO2013/065802, JP-A-2015-010162, etc. may be used.

As a method of ring-opening addition polymerization of the alkylene oxide to the initiator to obtain the oxyalkylene polymer A, known methods may be employed. For example, production methods disclosed in WO2011/125951, Japanese Patent No. 5648797, etc. may be employed.

<Oxyalkylene Polymer B>

The oxyalkylene polymer B is an oxyalkylene polymer having one hydroxy group per molecule and Mn of at least 5,000. The oxyalkylene polymer B preferably has Mn of higher than 5,000.

The oxyalkylene polymer B has one hydroxy group per molecule. The number of hydroxy groups in the oxyalkylene polymer B can be measured by $^{13}$C-NMR. Specifically, from a peak obtained by $^{13}$C-NMR, the type of the initiator is identified, and when the identified initiator is an initiator having one hydroxy group in one molecule, the oxyalkylene polymer B is confirmed to have one hydroxy group.

The oxyalkylene polymer B has a structure that at least one type of alkylene oxide is subjected to ring-opening addition to an initiator having one hydroxy group in one molecule.

The number of carbon atoms in the alkylene oxide is not particularly limited and is preferably from 2 to 5, more preferably from 2 to 3. When at least two types of alkylene oxide are subjected to ring-opening addition to the initiator, the arrangement of units derived from the respective alkylene oxides may be random or block.

As the alkylene oxide, it is preferred to use propylene oxide alone or propylene oxide and ethylene oxide in combination. When propylene oxide and ethylene oxide are used in combination, the molar ratio of propylene oxide and ethylene oxide is not particularly limited, and it is preferred that the content of ethylene oxide units in the oxyalkylene polymer B falls within the after-mentioned range. The higher the content of propylene oxide units is, the more the crystallinity of the oxyalkylene polymer B tends to decrease, and the higher the content of ethylene oxide units is, the more the hydrophilicity of the oxyalkylene polymer B improves.

The oxyalkylene polymer B may be two or more types.

The content of ethylene oxide units in the oxyalkylene polymer B is not particularly limited and is preferably from 0 to 80 mass %, more preferably from 0 to 60 mass %, further preferably from 5 to 55 mass %, still more preferably from 10 to 50 mass %. When the content of the ethylene oxide units in the oxyalkylene polymer B falls within the above range, a pressure-sensitive adhesive to be obtained will have more appropriate adhesion to the skin and moisture permeability.

The content of the ethylene oxide units in the oxyalkylene polymer B can be calculated in the same manner as in the oxyalkylene polymer A. When two or more types of oxyalkylene polymer B are contained, the content of ethylene oxide units as a value calculated by weighted average of them preferably falls within the above range.

Mn of the oxyalkylene polymer B is not particularly limited so long as it is higher than 5,000, and is preferably from 5,000 to 50,000, more preferably higher than 5,000 and at most 50,000, further preferably from 8,000 to 30,000. When Mn of the oxyalkylene polymer B is at least 5,000, the flexibility of a pressure-sensitive adhesive to be obtained and the followability to the skin when applied to the skin will be more favorable. When Mn of the oxyalkylene polymer B is higher than 5,000, the flexibility of an adhesive to be obtained will be further favorable. Further, the followability to the skin when applied to the skin will be further favorable.

Mw/Mn of the oxyalkylene polymer B is not particularly limited and is preferably less than 1.20, more preferably less than 1.13, particularly preferably less than 1.10. When the molecular weight distribution of the oxyalkylene polymer B is less than 1.20, the reactivity will be good, the after-mentioned polyurethane prepolymer can be more efficiently produced, and the polyurethane prepolymer to be obtained tends to have further low viscosity.

The degree of unsaturation of the oxyalkylene polymer B is preferably at most 0.015 meq/g, more preferably at most 0.013 meq/g, further preferably at most 0.008 meq/g. The degree of unsaturation of the oxyalkylene polymer B may be 0. When the degree of unsaturation of the oxyalkylene polymer B is at most the upper limit value, a prepolymer to be obtained will have more favorable curability, and adhesive residue to the skin will be further reduced. Mn of the oxyalkylene polymer B can be measured in the same manner as in the oxyalkylene polymer A.

In a case where two or more types of the oxyalkylene polymer B are contained, Mn, Mw/Mn and the degree of unsaturation of the respective oxyalkylene polymers B preferably fall within the above ranges.

The oxyalkylene polymer B is preferably produced by subjecting an alkylene oxide to ring-opening addition to an initiator having one hydroxy group in one molecule in the presence of a catalyst.

The initiator having one hydroxy group in one molecule for producing the oxyalkylene polymer B is preferably a $C_{2-4}$ monohydric alcohol, more preferably at least one member selected from the group consisting of propanol (n-propyl alcohol), 2-propanol (isopropyl alcohol), 1-butanol (n-butyl alcohol), 2-butanol (sec-butyl alcohol), 2-methyl-1-propanol (isobutyl alcohol) and 2-methyl-2-propanol (tert-butyl alcohol), further preferably at least one member selected from the group consisting of 1-butanol (n-butyl alcohol), 2-butanol (sec-butyl alcohol), 2-methyl-1-propanol (isobutyl alcohol) and 2-methyl-2-propanol (tert-butyl alcohol). The $C_{2-4}$ alcohol is available at a low cost, whereby the production cost of the oxyalkylene polymer B can be reduced.

As the catalyst, a DMC catalyst is preferably used in the same manner as in the case of the oxyalkylene polymer A. Reaction conditions such as reaction time are controlled so that an oxyalkylene polymer to be produced would have Mn of at least 5,000, since the oxyalkylene polymer B has Mn of at least 5,000.

<Diisocyanate Compound>

A diisocyanate compound used to obtain the hydroxy group-terminated polyurethane prepolymer of the present invention by being reacted with the above-mentioned oxyalkylene polymer A and the above-mentioned oxyalkylene polymer B is not particularly limited, so long as it is an organic compound having two isocyanate groups in one molecule.

The diisocyanate compound may be at least one member selected from the group consisting of an aliphatic diisocyanate compound, an alicyclic diisocyanate compound, an aromatic diisocyanate compound and an aromatic aliphatic diisocyanate compound.

The aliphatic diisocyanate compound may, for example, be a linear aliphatic diisocyanate such as tetramethylene diisocyanate, dodecamethylene diisocyanate or hexamethylene diisocyanate (HDI), or a branched aliphatic diisocyanate such as 2,2,4-trimethylhexamethylene diisocyanate, 2,4,4-trimethylhexamethylene diisocyanate, lysine diisocyanate, 2-methylpentane-1,5-diisocyanate or 3-methylpentane-1,5-diisocyanate, but the aliphatic diisocyanate compound is not limited thereto. The aliphatic diisocyanate compound is preferably the linear aliphatic diisocyanate, more preferably a $C_{4-8}$ linear aliphatic diisocyanate, further preferably hexamethylene diisocyanate (HDI), since a polyurethane (pressure-sensitive adhesive) to be obtained will have a higher glass transition temperature and will be more excellent in tensile strength and elongation at break.

The alicyclic diisocyanate compound may, for example, be isophorone diisocyanate, hydrogenated xylylene diisocyanate, 4,4'-dicyclohexylmethane diisocyanate, 1,4-cyclohexane diisocyanate, methylcyclohexylene diisocyanate or 1,3-bis(isocyanatomethyl)cyclohexane, but the alicyclic diisocyanate compound is not limited thereto. The alicyclic diisocyanate compound is preferably either one or both of isophorone diisocyanate and 4,4'-dicyclohexylmethane diisocyanate, more preferably isophorone diisocyanate, since a polyurethane (pressure-sensitive adhesive) to be obtained will have a higher glass transition temperature and will be more excellent in tensile strength and elongation at break.

The aromatic diisocyanate compound may, for example, be tolylene diisocyanate (TDI), 2,2'-diphenylmethane diisocyanate, 2,4'-diphenylmethane diisocyanate, 4,4'-diphenylmethane diisocyanate (MDI), 4,4'-dibenzyl diisocyanate, 1,5-naphthylene diisocyanate, xylylene diisocyanate, 1,3-phenylene diisocyanate or 1,4-phenylene diisocyanate, but the aromatic diisocyanate compound is not limited thereto. The aromatic diisocyanate compound is preferably diphenylmethane diisocyanate, more preferably 4,4'-diphenylmethane diisocyanate (MDI), since a polyurethane to be obtained will have a higher glass transition temperature.

The aromatic aliphatic diisocyanate compound may, for example, be dialkyldiphenylmethane diisocyanate, tetraalkyldiphenylmethane diisocyanate or α,α,α,α-tetramethylxylylene diisocyanate, but the aromatic aliphatic diisocyanate compound is not limited thereto. The aromatic aliphatic diisocyanate compound is preferably α,α,α,α-tetramethyxylylene diisocyanate, since a polyurethane to be obtained will be more excellent in elongation at break.

The diisocyanate compound used for producing the hydroxy group-terminated polyurethane prepolymer is preferably at least one member selected from the group consisting of an aliphatic diisocyanate compound and an alicyclic diisocyanate compound, more preferably an aliphatic diisocyanate compound, further preferably a $C_{4-6}$ aliphatic diisocyanate compound, still more preferably at least one member selected from the group consisting of HDI and modified products thereof, further preferably HDI or an isocyanurate modified product of HDI, since a polyurethane to be obtained will be more excellent in tensile strength and the elongation at break.

As the diisocyanate compound for producing the hydroxy group-terminated polyurethane prepolymer of the present invention, a bifunctional isocyanate group-terminated polyurethane prepolymer which is a prepolymer formed by reacting the above-mentioned aliphatic diisocyanate compound, alicyclic diisocyanate compound, aromatic diisocyanate compound or aromatic aliphatic diisocyanate compound with a diol, may be used.

The diol for producing the isocyanate group-terminated polyurethane prepolymer may, for example, be ethylene glycol, propylene glycol, 1,4-butanediol, 1,5-pentanediol, 3-methyl-1,5-pentanediol or 1,6-hexanediol, but the diol is not limited thereto. The diol is preferably at least one member selected from the group consisting of ethylene glycol, propylene glycol, 1,4-butanediol, 1,5-pentanediol, 3-methyl-1,5-pentanediol and 1,6-hexanediol, more preferably propylene glycol, since a polyurethane (pressure-sensitive adhesive) to be obtained will have a higher glass transition temperature.

The isocyanate index when producing the isocyanate group-terminated polyurethane prepolymer is higher than 100. The isocyanate index is a value obtained by dividing the number of moles of isocyanate groups in the diisocyanate compound by the number of moles of hydroxy groups in the diol and multiplying the quotient by 100.

The commercially available product of the bifunctional isocyanate group-terminated polyurethane prepolymer may, for example, be Duranate D101, Duranate D201 and Duranate A201 H (manufactured by Asahi Kasei Corporation respectively), but the product is not limited thereto.

<Method for Producing Hydroxy Group-Terminated Polyurethane Prepolymer>

The method for producing the hydroxy group-terminated polyurethane prepolymer of the present invention is not particularly limited, and a method of reacting the oxyalkylene polymer A and the oxyalkylene polymer B with the diisocyanate compound at a ratio so that the isocyanate index would be less than 100, may be mentioned. The isocyanate index is a value obtained by dividing the number of moles of isocyanate groups in the diisocyanate compound by the total number of moles of hydroxy groups in the oxyalkylene polymer A and the oxyalkylene polymer B, and multiplying the quotient by 100.

The content of the oxyalkylene polymer A to the total mass of the oxyalkylene polymer A and the oxyalkylene polymer B is not particularly limited, and is preferably from 10 to 95 mass %, more preferably from 20 to 80 mass %. When the content of the oxyalkylene polymer A to the total mass of the oxyalkylene polymer A and the oxyalkylene polymer B falls within the above range, balance of the moisture permeability of a pressure-sensitive adhesive to be obtained and adhesion to the skin and to a substrate will be maintained good.

The average number of hydroxy groups in the hydroxy group-terminated polyurethane prepolymer is preferably less than 3.0, more preferably from 1.7 to 2.9, further preferably from 1.7 to 2.5, particularly preferably from 1.8 to 2.4. When the average number of hydroxy groups in the hydroxy group-terminated polyurethane prepolymer falls within the above range, balance of the moisture permeability of a pressure-sensitive adhesive to be obtained and adhesion to the skin and to a substrate will be maintained good.

"Average number of hydroxy groups f" of the hydroxy group-terminated polyurethane prepolymer is a value obtained by the following formula (I):

$$f=(1{,}000\,f_n/Mn)/[\{(1{,}000/Mn)-(\text{degree of unsaturation}/f_n)\}+\text{degree of unsaturation}] \quad (I)$$

wherein $f_n$ is the number of active hydrogen atoms per molecule of the initiator used as a starting material for producing the oxyalkylene polymer.

Further, "average number of functional groups $f_{ave}$" in a case where a plurality of oxyalkylene polymers are used in combination can be calculated by the following formula (II):

$$f_{ave}=\Sigma(f_i \times W_i/Mn_i)/\Sigma(W_i/Mn_i) \quad (II)$$

wherein $f_i$ is the number of active hydrogen atoms per molecule of the initiator used as a starting material for each of the oxyalkylene polymers, $W_i$ is a part by mass of each of the oxyalkylene polymers, and $Mn_i$ is Mn of each of the oxyalkylene polymers.

As the case requires, a catalyst may be used in the production of the hydroxy group-terminated polyurethane prepolymer of the present invention.

The catalyst is preferably at least one member selected from a tertiary amine compound and an organic metal compound.

The tertiary amine compound may, for example, be triethylamine, triethylenediamine and 1,8-diazabicyclo(5,4,0)-undecene-7 (DBU), but the tertiary amine compound is not limited thereto.

The organic metal compound is preferably at least one member selected from a tin compound and a non-tin compound.

The tin compound may, for example, be dibutyltin dichloride, dibutyltin oxide, dibutyltin dibromide, dibutyltin dimaleate, dibutyltin dilaurate (DBTDL), dibutyltin diacetate, dibutyltin sulfide, tributyltin sulfide, tributyltin oxide, tributyltin acetate, triethyltin ethoxide, tributyltin ethoxide, dioctyltin oxide, tributyltin chloride, tributyltin trichloroacetate or tin 2-ethylhexanate, but the tin compound is not limited thereto.

The non-tin compound may, for example, be a titanium compound such as dibuyltitanium dichloride, tetrabutyltitanate or butoxytitianium trichloride, a lead compound such as lead oleate, lead 2-ethylhexanoate, lead benzoate and lead naphthenate, an iron compound such as iron 2-ethylhexanoate or iron acetylacetonate, a cobalt compound such as cobalt benzoate or cobalt 2-ethylhexanoate, a zinc compound such as zinc naphthenate or zinc 2-ethylhexanoate, or a zirconium compound such as zirconium naphthenate.

One type of a catalyst may be used alone, or two or more types may be used in combination.

In a case where the catalyst is used, the amount of the catalyst to be used is not particularly limited, and is preferably from 0.01 to 1.0 part by mass per 100 parts by mass of the total amount of the oxyalkylene polymer A, the oxyalkylene polymer B and the diisocyanate compound.

As the case requires, a solvent may be used for the production of the hydroxy group-terminated polyurethane prepolymer of the present invention.

The solvent is preferably at least one member selected from a ketone such as acetone and methyl ethyl ketone, an ester such as ethyl acetate and an aromatic hydrocarbon such as toluene and xylene.

Two or more types of solvent may be used in combination.

In a case where the solvent is used, the amount of the solvent to be used is not particularly limited and is preferably from 50 to 500 parts by mass per 100 parts by mass of the total amount of the oxyalkylene polymer and the diisocyanate compound.

The method for producing the hydroxy-group terminated polyurethane prepolymer of the present invention may, for example, be the following methods.

Production method 1: A method of charging the diisocyanate compound, the oxyalkylene polymer A, the oxyalkylene polymer B, the catalyst and the solvent all at once in a flask.

Production method 2: A method of charging the oxyalkylene polymer A, the oxyalkylene polymer B, the catalyst and the solvent in a flask and dropwise adding the diisocyanate compound thereto.

Among these methods, the production method 2 is preferred, since a low molecular component among starting materials can be reacted by priority, the molecular weight distribution can be made narrow, and reaction control is easy.

The reaction temperature is preferably lower than 100° C., more preferably from 85 to 95° C. When the reaction temperature is lower than 100° C., side reactions other than the urethane reaction are easily suppressed, and the desired prepolymer can be easily obtained.

The isocyanate index when producing the hydroxy group-terminated polyurethane prepolymer of the present invention is preferably from 30 to 95, more preferably from 40 to 95, further preferably from 50 to 95. When the isocyanate index falls within the above range, a hydroxy group-terminated polyurethane prepolymer having an appropriate molecular chain length can be produced, and the productivity thereby improves.

After the termination of the reaction, a reaction terminator is preferably added to inactivate the catalyst. The reaction terminator may, for example, be acetylacetone, but the reaction terminator is not limited thereto. Two or more types of the reaction terminator may be used in combination.

<Content of Ethylene Oxide Units in Hydroxy Group-Terminated Polyurethane Prepolymer>

The content of ethylene oxide units in the hydroxy group-terminated polyurethane prepolymer of the present invention is at least 10 mass %, preferably from 10 to 80 mass %, more preferably from 12 to 50 mass %. When the content of ethylene oxide units in the hydroxy group-terminated polyurethane prepolymer of the present invention is at least 10 mass %, a pressure-sensitive adhesive to be obtained will have both a low adhesion to the skin and a high adhesion to a substrate.

[Pressure-Sensitive Adhesive]

The pressure-sensitive adhesive of the present invention is a pressure-sensitive adhesive which is obtained by reacting the oxyalkylene polymer A having an average number of hydroxy groups per molecule of from 2.1 to 3, the oxyalkylene polymer B having one hydroxy group per molecule and a number average molecular weight of at least 5,000 and the polyisocyanate compound, having a content of ethylene oxide units of at least 10 mass %, or a pressure-sensitive adhesive obtained by reacting the hydroxy group-terminated polyurethane prepolymer of the present invention and a curing agent containing a polyisocyanate compound having at least three isocyanate groups in one molecule (hereinafter referred to simply as "curing agent").

The polyisocyanate compound is a compound having at least two isocyanate groups in one molecule, and is the above-mentioned diisocyanate compound or the after-mentioned polyisocyanate compound having at least three isocyanate groups in one molecule.

The content of ethylene oxide units in the pressure-sensitive adhesive of the present invention is at least 10 mass %, preferably from 10 to 80 mass %, more preferably from 12 to 50 mass %. When the content of ethylene oxide units in the pressure-sensitive adhesive of the present invention is at least 10 mass %, the moisture permeability is good, the adhesion to a highly polar substrate improves, and keratin is hardly released in the wet state.

The storage elastic modulus at 25° C. of the pressure-sensitive adhesive of the present invention is preferably from $1.0 \times 10^4$ Pa to $5.0 \times 10^5$ Pa, more preferably from $2.0 \times 10^4$ Pa to $4.8 \times 10^5$ Pa, further preferably from $2.0 \times 10^4$ to $3.0 \times 10^5$ Pa, particularly preferably from $2.0 \times 10^4$ Pa to $2.5 \times 10^5$ Pa, most preferably from $2.0 \times 10^4$ Pa to $1.0 \times 10^5$ Pa.

When the storage elastic modulus of the pressure-sensitive adhesive of the present invention falls within the above range, the adhesion to the skin is more favorable, adhesive residue will not remain, and more favorable adhesion to the skin can be obtained.

The storage elastic modulus at 80° C. of the pressure-sensitive adhesive of the present invention is preferably at most $4.0 \times 10^5$ Pa, preferably at least $5.0 \times 10^2$ Pa and less than $3.0 \times 10^5$ Pa, more preferably from $1.0 \times 10^3$ Pa to $6.0 \times 10^4$ Pa, further preferably from $1.0 \times 10^3$ Pa to $4.0 \times 10^4$ Pa, particularly preferably from $2.0 \times 10^3$ Pa to $1.0 \times 10^4$ Pa. When the storage elastic modulus of the pressure-sensitive adhesive of the present invention falls within the above range, the adhesion to the skin is more favorable, adhesive residue will not remain, and a more favorable adhesion to the skin can be obtained.

<Method for Producing Pressure-Sensitive Adhesive>

The method for producing the pressure-sensitive adhesive by reacting the hydroxy group-terminated polyurethane prepolymer of the present invention and a curing agent will be described.

The curing agent may contain a polyisocyanate compound (diisocyanate compound) having two isocyanate groups in one molecule in addition to the polyisocyanate compound having at least three isocyanate groups in one molecule.

As the diisocyanate compound, the above-mentioned diisocyanate compound and the above-mentioned bifunctional isocyanate group-terminated polyurethane prepolymer may be mentioned. As the polyisocyanate compound having at least three isocyanate groups in one molecule, an isocyanurate modified product of the above-mentioned diisocyanate compound, a biuret modified product of the above-mentioned diisocyanate compound, an allophanate modified product of the above-mentioned diisocyanate compound and a trifunctional or higher functional isocyanate group-terminated polyurethane prepolymer (adduct modified product) obtained by reacting the above-mentioned diisocyanate compound and a polyol having at least 3 hydroxy groups in one molecule are mentioned. The isocyanurate modified product may, for example, be Coronate HX (manufactured by Tosoh Corporation). The biuret modified product may, for example, be Duranate 24A-100 (manufactured by Asahi Kasei Corporation). The commercially available product of the trifunctional or higher functional isocyanate group-terminated polyurethane prepolymer may, for example, be Coronate L, Coronate L-55E or Coronate L-45E (manufactured by Tosoh Corporation respectively), but the commercially available product is not limited thereto.

The isocyanate index when producing the pressure-sensitive adhesive of the present invention by reacting the hydroxy group-terminated polyurethane prepolymer and the curing agent is higher than 100, more preferably from 105 to 160. The isocyanate index is a value obtained by dividing the number of moles of isocyanate groups in the curing agent by the number of moles of hydroxy groups in the hydroxy group-terminated polyurethane prepolymer, and multiplying the quotient by 100.

As the case requires, a catalyst may be used when producing the pressure-sensitive adhesive of the present invention by reacting the hydroxy group-terminated polyurethane prepolymer and the curing agent. The catalyst is preferably the above-mentioned catalyst. Further, the amount of the catalyst used is preferably from 0.01 to 1.0 part by mass, per 100 parts by mass of the total amount of the hydroxy group-terminated polyurethane prepolymer and the curing agent. After the termination of the reaction, a reaction terminator is preferably added to inactivate the catalyst.

As the case requires, a solvent may be used when producing the pressure-sensitive adhesive of the present invention by reacting the hydroxy group-terminated polyurethane prepolymer and the curing agent. The type of the solvent is preferably the above-mentioned solvent. Further, the amount of the solvent used is preferably from 50 to 500 part by mass, per 100 parts by mass of the total amount of the hydroxy group-terminated prepolymer and the curing agent.

The temperature when reacting the hydroxy group-terminated polyurethane prepolymer and the curing agent is preferably lower than 100° C., more preferably from 85 to 95° C.

The method for producing a pressure-sensitive adhesive by reacting the oxyalkylene polymer A, the oxyalkylene polymer B and the polyisocyanate compound will be described.

The polyisocyanate compound in this production method may be selected from a polyisocyanate compound having two isocyanate groups in one molecule and a polyisocyanate compound having at least three isocyanate groups in one molecule. For example, as the polyisocyanate compound to be reacted with the oxyalkylene polymer A and the oxyalkylene polymer B, at least one type of the above-mentioned diisocyanate compound and the above-mentioned polyisocyanate compound to be used as the curing agent may be used.

The isocyanate index in this production method is higher than 100, more preferably from 105 to 160. The isocyanate index is a value obtained by dividing the number of moles of isocyanate groups in the polyisocyanate compound by the total number of moles of hydroxy groups in the oxyalkylene polymer A and the oxyalkylene polymer B, and multiplying the quotient by 100.

As the case requires, a catalyst may be used when producing the pressure-sensitive adhesive of the present invention by reacting the oxyalkylene polymer A, the oxyalkylene polymer B and the polyisocyanate compound. The catalyst is preferably the above-mentioned catalyst. Further, the amount of the catalyst to be used is preferably from 0.01 to 1.0 part by mass, per 100 parts by mass of the total amount of the oxyalkylene polymer A, the oxyalkylene polymer B and the polyisocyanate compound. After the termination of the reaction, a reaction terminator is preferably added to inactivate the catalyst.

As the case requires, a solvent may be used when producing the pressure-sensitive adhesive of the present invention by reacting the oxyalkylene polymer A, the oxyalkylene polymer B and the polyisocyanate compound. The solvent is preferably the above-mentioned solvent. Further, the amount of the solvent to be used is preferably from 50 to 500 parts by mass, per 100 parts by mass of the total amount of the oxyalkylene polymer A, the oxyalkylene polymer B and the polyisocyanate compound.

The temperature when reacting the oxyalkylene polymer A, the oxyalkylene polymer B and the polyisocyanate compound is preferably lower than 100° C., more preferably from 85 to 95° C.

<Components which May Be Blended in Pressure-Sensitive Adhesive>

In the pressure-sensitive adhesive of the present invention, at least one additive of a plasticizer, an antioxidant, an antistatic agent, a filler, a ultraviolet absorber, a light stabilizer, a leveling agent, etc. may be blended.

The plasticizer is not particularly limited and is preferably a $C_{8-30}$ fatty acid ester, a phosphoric acid ester or the like, from the viewpoint of compatibility with other components. When the pressure-sensitive adhesive of the present invention contains a plasticizer, the wettability of the pressure-sensitive adhesive to an adhered object will improve.

The $C_{8-30}$ fatty acid ester may, for example, be an ester of a branched alcohol having at most 18 carbon atoms with a $C_{6-18}$ monobasic acid or polybasic acid, an ester of a tetrahydric or lower alcohol with a $C_{14-18}$ unsaturated fatty acid or branched fatty acid, an ester of a polyalkylene glycol with a $C_{6-18}$ monobasic acid or polybasic acid, or a fatty acid ester of which unsaturated moiety is epoxidized with a peroxide or the like.

The phosphoric acid ester may, for example, be an ester compound of a $C_{2-18}$ linear or branched alcohol with phosphorus acid or phosphoric acid.

The antioxidant is not particularly limited and is preferably a phenolic antioxidant, an amine type antioxidant, a sulfur type antioxidant or a phosphoric acid type antioxidant, more preferably a phenolic antioxidant since skin sensitivity is low. When the pressure-sensitive adhesive of the present invention contains an antioxidant, heat deterioration of the pressure-sensitive adhesive can be suppressed.

As specific examples of the phenolic antioxidant, a monophenolic antioxidant such as 2,6-di-t-butyl-p-cresol, a bisphenolic antioxidant such as 2,2'-methylene bis(4-methyl-6-t-butylphenol) and a high molecular phenolic antioxidant such as 1,1,3-tris(2-methyl-4-hydroxy-5-t-butylphenyl)butane may be mentioned.

As specific examples of the amine type antioxidant, bis(2,2,6,6-tetramethyl-4-piperidyl) sebacate, a polycondensate of dimethyl succinate and 1-(2-hydroxyethyl)-4-hydroxy-2,2,6,6-tetramethyl piperidine ethanol, N,N',N",N"'-tetrakis-(4,6-bis-(butyl-(N-methyl-2,2,6,6-tetramethylpiperidin-4-yl)amino)-triazin-2-yl)-4,7-diazadecane-1,10-diamine and a polycondensate of dibutylamine 1,3,5-triazine N,N'-bis(2,2,6,6-tetramethyl-4-piperidyl)-1,6-hexamethylene diamine and N-(2,2,6,6-tetramethyl-4-piperidyl)butylamine may be mentioned.

As specific examples of the sulfur type antioxidant, dilauryl 3,3'-thiodipropionate, dimyristyl 3,3'-thiodipropionate and distearyl 3,3'-thiodipropionate may be mentioned.

As specific examples of the phosphorus antioxidant, triphenyl phosphite, diphenyl isodecyl phosphite and phenyl diisodecyl phosphite may be mentioned.

The antistatic agent is not particularly limited and may be an inorganic salt, an ionic liquid or a surfactant. When the pressure-sensitive adhesive of the present invention contains an antistatic agent, electrostatic discharge can be suppressed, and for example, breakage of an electronic component incorporated in a wearable device can be prevented.

The inorganic salt may, for example, be sodium chloride, potassium chloride, lithium chloride, lithium perchlorate, ammonium chloride, potassium chlorate, aluminum chloride, copper chloride, ferrous chloride, ferric chloride, ammonium sulfate, potassium nitrate, sodium nitrate, sodium carbonate and sodium thiocyanate.

The ionic liquid is a salt of a cation and an anion, and the cation may, for example, be preferably imidazolium ion, pyridinium ion or ammonium ion.

As the surfactant, a nonionic surfactant such as a glycerin fatty acid ester, an anionic surfactant such as an alkyl sulfonate, a cationic surfactant such as a tetraalkyl ammonium salt and an amphoteric surfactant may be mentioned.

The filler may, for example, be talc, calcium carbonate or titanium oxide.

The ultraviolet absorber may, for example, be a benzophenone type ultraviolet absorber, a benzotriazole type ultraviolet absorber, a salicylic acid type ultraviolet absorber, an oxanilide type ultraviolet absorber, a cyanoacrylate type ultraviolet absorber or a triazine type ultraviolet absorber.

The light stabilizer may, for example, be a hindered amine light stabilizer or a ultraviolet light stabilizer.

The hindered amine light stabilizer may, for example, be [bis(2,2,6,6-tetramethyl-4-piperidyl) sebacate], bis(1,2,2,6,6-pentamethyl-4-piperidyl) sebacate or methyl 1,2,2,6,6-pentamethyl-4-piperidyl sebacate, but the hindered amine light stabilizer is not limited thereto.

The ultraviolet stabilizer may, for example, be nickel bis(octylphenyl)sulfide, [2,2'-thiobis(4-tert-ocytylphenolate)]-n-butylamine nickel, nickel complex-3,5-di-tert-butyl-4-hydroxybenzyl-phosphoric acid monoethylate, nickel-dibutyl dithiocarbamate, a benzoate type quencher or nickel dibutyl dithiocarbamate, but the ultraviolet light stabilizer is not limited thereto.

<Moisture Permeability>

The moisture permeability of the pressure-sensitive adhesive of the present invention is preferably at least 3,000 g/m²·day, more preferably at least 3,500 g/m²·day, further preferably at least 4,000 g/m²·day. The upper limit of the moisture permeability is not particularly limited.

The moisture permeability of the pressure-sensitive adhesive of the present invention is obtained as an amount of water vapor which passes through a test specimen per 1 m² per one day.

A test specimen is prepared as described below.

The hydroxy group-terminated polyurethane prepolymer or a mixture of the oxyalkylene polymer A, the oxyalkylene polymer B and the curing agent is applied on a polyester film to which release treatment is applied (release body, thickness of 50 μm) by a knife coater so that the dry film thickness would be 25 μm, followed by dry-curing at 100° C. for 3 minutes to form a pressure-sensitive adhesive layer on the release body. A rough nylon net which has no influence over the moisture permeability of the pressure-sensitive adhesive is attached, to the obtained pressure-sensitive adhesive layer, and stored in a hot air dryer under an atmosphere of 50° C. for 3 days to complete the crosslinking reaction of the pressure-sensitive adhesive layer, and the release body is released to prepare a test specimen.

As the measurement of the moisture permeability, under an atmosphere of 40° C., the relative humidity of one side space separated by the test specimen is set to 90%, the other side space is kept in a dry state by a moisture absorbent, and the mass (g) of water vapor which passes through the test specimen in 24 hours (one day) is measured and converted to a value per 1 m² of the test material. The measurement is carried out in accordance with JIS Z0208: 1976 "Testing methods for Determination of the Water Vapor Transmission Rate of Moisture-Proof Packaging Materials (Dish Method)". A cup containing about 50 g of a calcium chloride moisture absorbent is covered with a disk shape test specimen having a diameter larger by about 10 mm than the inner diameter of the cup, the test specimen is fixed by a rubber packing and a ring, and the cup is screwed up. The total mass of the test specimen is measured, and the cup is put in a thermo-hygrostat at 40° C. under a 90% RH atmosphere, the change of the mass is measured at constant intervals, and the moisture permeability is measured in accordance with the following formula.

Moisture permeability(g/m²·day)=W×240,000/S wherein S is a moisture permeation area (cm²), and W is a mass increase per hour (g/hr).

<Adhesion to Phenol Resin>

The adhesion of the pressure-sensitive adhesive of the present invention to a phenol resin is preferably at least 2.5 N/15 mm, more preferably at least 3 N/15 mm.

The adhesion of the pressure-sensitive adhesive of the present invention to a phenol resin is an adhesion measured in accordance with the test method stipulated in JIS Z0237: 2009 "Test methods of pressure-sensitive adhesive tapes and sheets, 10 Adhesion", as follows. A test specimen having a width of 15 mm is attached to a Bakelite panel (phenol resin board, manufactured by Sumitomo Bakelite Co., Ltd., PL-1102) under an atmosphere of 25° C., pressure-bonded by reciprocating a 2 kg rubber roll once at a rate of 300 mm/min and left to stand for 20 minutes, and the peel strength at a peel angle of 90° or 180° at a peel rate of 300 mm/min is measured.

<Adhesion to Human Skin>

The adhesion of the pressure-sensitive adhesive of the present invention to the human skin is preferably from 0.2 to 1 N/15 mm, more preferably from 0.3 to 0.7 N/15 mm.

The adhesion of the pressure-sensitive adhesive of the present invention to the human skin is an adhesion obtained in the same manner as in the above method for measuring the adhesion to a phenol resin, except that instead of the Bakelite panel, the back of a human hand is used. The back of a human hand is degreased with isopropyl alcohol and air-dried for use.

<Difference Between Adhesion to Phenol Resin and Adhesion to Human Skin>

The difference in the adhesion of the pressure-sensitive adhesive of the present invention between to a phenol resin and to the human skin is preferably at least 2 N/15 mm, more preferably at least 2.5 N/15 mm.

The difference between the adhesion to a phenol resin and the adhesion to the human skin is calculated by the following formula.

"Difference between adhesion to a phenol resin and adhesion to the human skin"="adhesion to a phenol resin"−"adhesion to the human skin"

[Two-Part Pressure-Sensitive Adhesive]

The pressure-sensitive adhesive of the present invention may be a two-part pressure-sensitive adhesive comprising a first agent containing the hydroxy group-terminated polyurethane prepolymer of the present invention and a second agent containing a polyisocyanate compound having at least three isocyanate groups in one molecule.

By mixing the first agent and the second agent, the formation of urethane bonds proceeds, and a pressure-sensitive adhesive containing a polyurethane is thereby obtained.

The second agent containing a polyisocyanate compound having at least three isocyanate groups in one molecule is the same as the above-mentioned curing agent.

The first agent or the second agent may further contain a catalyst, a solvent, the above-mentioned components which may be blended in the pressure-sensitive adhesive, etc.

The first agent and the second agent are stored in separate containers. As the containers, various containers such as a tube and a bottle may be used.

The form of selling the two-part pressure-sensitive adhesive of the present invention may be a form comprising the first agent and the second agent or may be a form comprising the first agent and no second agent. In the case of the form of selling comprising no second agent, a curing agent separately prepared by a user may be used, whereby the degree of freedom for a user is high.

[Adhesive Skin Patch]

The adhesive skin patch of the present invention comprises a substrate and a pressure-sensitive adhesive layer containing the pressure-sensitive adhesive of the present invention formed on a surface of the substrate.

The adhesive skin patch of the present invention preferably has the pressure-sensitive adhesive layer formed on one surface of a substrate film and a release liner releasably laminated to cover an adhesive surface of the pressure-sensitive adhesive layer.

The thickness of the substrate film is not particularly limited and is preferably from 1 to 9 μm, more preferably from 3 to 9 μm. When the thickness of the substrate film falls within the above range, the possibility of breakage of the adhesive skin patch can be low, and the followability of the adhesive skin patch to the skin surface can be secured. The material of the substrate film is not particularly limited and may, for example, be a polyurethane polymer such as a polyether urethane or a polyester urethane, an amide polymer such as a polyether polyamide block polymer, an acrylic polymer such as a polyacrylate, an olefin polymer such as a polyethylene, a polypropylene or an ethylene/vinyl acetate copolymer, or an ester polymer such as a polyether polyester. The material of the substrate film is preferably a polyurethane polymer or an amide polymer from the viewpoint of the moisture permeability. As the material of the substrate film, one type may be used alone, or two or more types may be used in combination, Further, a laminated film comprising laminated substrate films made of different materials may be used. The substrate film may be laminated with a cloth such as woven fabric, non-woven fabric, knitted cloth or net. The thickness of the pressure-sensitive adhesive layer is not particularly limited and is preferably from 10 to 50 μm, more preferably from 15 to 35 μm. When the thickness of the pressure-sensitive adhesive layer falls within the above range, the adhesion of the pressure-sensitive adhesive layer to the skin surface will be more favorable.

It is preferred to cover the pressure-sensitive adhesive layer surface of the adhesive skin patch of the present invention with a release liner until use in order to prevent the surface of the pressure-sensitive adhesive layer from being contaminated. As the release liner, one commonly used for the skin or for an pressure-sensitive adhesive tape to be attached to the skin may be used. Specifically, woodfree paper, glassine paper, parchment paper, etc. coated with a release agent having a release property, such as a silicone resin or a fluororesin, woodfree paper anchor-coated with a resin, or polyethylene-laminated woodfree paper etc., coated with a release agent having a release property, such as a silicone resin or a fluororesin, may be used.

On the adhesive skin patch of the present invention, a support film may be releasably laminated on the opposite side of the substrate film from the pressure-sensitive adhesive layer. The material of the support film is not particularly limited and is preferably a plastic film or paper. Particularly, a plastic film having transparency can be attached to the skin while viewing a place to be attached via the adhesive skin patch, and its usefulness is particularly significant when fixing a medical tool such as a catheter. To releasably bond the support film to a back surface of the substrate film, a method such as blown film extrusion, extrusion lamination, laminating or casting may be used. The thickness of the support film varies depending on materials, and is usually preferably from about 15 to about 200 μm, more preferably from about 20 to about 100 μm.

[Pressure-Sensitive Adhesive Tape]

The pressure-sensitive adhesive tape of the present invention comprises a substrate and a pressure-sensitive adhesive layer containing the pressure-sensitive adhesive of the present invention, formed on at least one surface of the substrate.

The pressure-sensitive adhesive tape of the present invention may have the pressure-sensitive adhesive layer on one surface of the substrate or on both surfaces of the substrate.

According to one form, the pressure-sensitive adhesive tape of the present invention preferably has the pressure-sensitive adhesive layer formed on one surface of the substrate film and has a release liner releasably laminated to cover an adhesive surface of the pressure-sensitive adhesive layer. This form is specifically referred to as "single-sided pressure-sensitive adhesive tape".

The substrate film and the release liner are the same as those in the adhesive skin patch of the present invention. Further, the thickness of the pressure-sensitive adhesive layer is the same as the thickness of the pressure-sensitive adhesive layer in the adhesive skin patch of the present invention.

This form of the pressure-sensitive adhesive tape can be used for fixing on a skin surface, an article to be fixed on a skin surface so that at least a part of the article to be fixed on a skin surface would be covered with the pressure-sensitive adhesive tape.

According to another form, the pressure-sensitive adhesive tape of the present invention preferably has pressure-sensitive adhesive layers formed on both surfaces of the substrate film and release liners releasably laminated to cover adhesive surfaces of the pressure-sensitive adhesive layers. This form is specifically referred to as "double-sided pressure-sensitive adhesive tape".

The substrate film and the release liner are the same as those in the adhesive skin patch of the present invention. Further, the thickness of the pressure-sensitive adhesive layer is the same as the thickness of the pressure-sensitive adhesive layer in the adhesive skin patch of the present invention.

This form of the pressure-sensitive adhesive layer can be used for fixing on a skin surface, an article to be fixed on a skin surface so that the pressure-sensitive adhesive tape is present between at least a part of a portion in contact with the skin surface of the article to be fixed on a skin surface and the skin surface.

According to still another form, the pressure-sensitive adhesive tape of the present invention preferably has a pressure-sensitive adhesive layer formed on one surface of a releasable substrate film and has a release liner releasably laminated to cover an adhesive surface of the pressure-sensitive adhesive layer. This form is specifically referred to as "pressure-sensitive adhesive transfer tape".

The releasable substrate film is preferably a substrate film which can be used for the adhesive skin patch of the present invention, coated with a release agent having a release property, such as a silicone resin or a fluororesin. The release liner is the same as that in the adhesive skin patch of the present invention. Further, the thickness of the pressure-sensitive adhesive layer is the same as the thickness of the pressure-sensitive adhesive layer in the adhesive skin patch of the present invention.

This form of the pressure-sensitive adhesive tape can be used for fixing on a skin surface, an article to be fixed on a skin surface so that the pressure-sensitive adhesive layer is present between at least a part of a portion in contact with the skin surface of the article to be fixed on a skin surface and the skin surface. The pressure-sensitive adhesive layer alone is present between the article to be fixed on a skin surface and the skin surface and no substrate film is present, whereby the adhesion of the article to the skin surface will be good.

[Wearable Device and Wearable Device Kit]

The wearable device of the present invention comprises a wearable device body and a pressure-sensitive adhesive layer containing the pressure-sensitive adhesive of the present invention, formed on at least a part of an adherend surface of the wearable device body.

Further, the wearable device kit of the present invention comprises a wearable device body and the pressure-sensitive adhesive of the present invention, the adhesive skin patch of the present invention or the pressure-sensitive adhesive tape of the present invention, for attaching the wearable device body to the skin of mammals.

The wearable device is not particularly limited and may, for example, be a sensor for heartbeat, heartbeat fluctuation, cardiac cycle, heartbeat wave form, cardiac potential, myoelectric activity, active mass, blood pressure, body temperature, electroencephalogram, electroencephalogram interval, respiration interval or the like.

The thickness of the pressure-sensitive adhesive layer to be formed at least at a part of an adherend surface of the wearable device body is not particularly limited and is preferably from 10 to 50 μm, more preferably from 15 to 40 μm. When the thickness of the pressure-sensitive adhesive layer falls within the above range, the wearable device body hardly drops when attached to the skin, and the attached surface will be less damaged when removing the wearable device body from the skin.

The wearable device body can be attached to the skin by using the adhesive skin patch of the present invention or the pressure-sensitive adhesive tape of the present invention.

The wearable device can be attached to the skin in such a state that the wearable device body is sandwiched between the adhesive skin patch and the skin.

In a case where the pressure-sensitive adhesive tape is a single-sided pressure-sensitive adhesive tape, the wearable device can be attached to the skin in such a state that the wearable device body is sandwiched between the pressure-sensitive adhesive tape and the skin.

In a case where the pressure-sensitive adhesive tape is a double-sided tape, the wearable device can be attached to the skin in such a state that the pressure-sensitive adhesive tape is present between the wearable device body and the skin.

In a case where the pressure-sensitive adhesive tape is a pressure-sensitive adhesive transfer tape, the wearable device can be attached to the skin in such a state that the pressure-sensitive adhesive layer is transferred to at least a part of an adherend surface of the wearable device body so that only the pressure-sensitive adhesive layer is present between the wearable device body and the skin.

The skin is preferably the skin of mammals, more preferably the skin of land mammals, further preferably the skin of human. The skin of human may include labial mucosa.

EXAMPLES

Now, the present invention will be described in further detail with reference to Examples. However, it should be understood that the present invention is by no means restricted to such Examples, and various modifications can be applied, so long as the gist of the present invention is not changed.

[Preparation of Oxyalkylene Polymer]

Preparation Example 1: Preparation of Polymer A1

Glycerin was used as an initiator.

First, 1,000 g of the initiator and a TBA-DMC catalyst slurry were added in a pressure resistant reaction container to prepare a reaction liquid. The amount of the TBA-DMC catalyst slurry added was adjusted so that the concentration of metals in the TBA-DMC catalyst in the reaction liquid would be 46 ppm.

Then, after the inside of the pressure resistant reaction container was replaced with nitrogen, the reaction liquid was heated with stirring, heating was terminated when the temperature reached 135° C., and while stirring was continued, 120 g (12 parts by mass per 100 parts by mass of the initiator) of propylene oxide was supplied in the pressure resistant reaction container and reacted.

After the temperature increase of the reaction liquid stopped, the reaction liquid was cooled to 135° C., and while stirring the reaction liquid, 4,728 g of propylene oxide was supplied in the pressure resistant reaction container. After confirming the termination of the reaction as the change of the internal pressure stopped, a step of neutralizing and removing the catalyst was carried out with a synthetic adsorbent (KYOWAAD 600S, manufactured by Kyowa Chemical Industry Co., Ltd.).

The number of hydroxy groups, the hydroxy value, Mn, Mw/Mn, the degree of unsaturation and the content of oxyethylene units (hereinafter referred to as "EO units") of the polymer A1 thus obtained are shown in Table 1. Here, these values are values measured by the above described methods. Values of polymers obtained by the following Preparation Examples are also shown in Table 1.

Preparation Example 2: Preparation of Polymer A2

A polymer A2 was prepared in the same manner as in Preparation Example 1, except that 20 mass % of propylene oxide was changed to ethylene oxide.

Preparation Example 3: Preparation of Polymer A3

A polymer A3 was prepared in the same manner as in Preparation Example 1, except that 80 mass % of propylene oxide was changed to ethylene oxide.

Preparation Example 4: Preparation of Polymer A4

A polymer A4 was prepared in the same manner as in Preparation Example 1, except that propylene glycol was used as the initiator, instead of glycerin.

Preparation Example 5: Preparation of Polymer A5

A polymer A5 was prepared in the same manner as in Preparation Example 2, except that propylene glycol was used as the initiator, instead of glycerin.

Preparation Example 6: Preparation of Polymer B1

A polymer B1 was prepared in the same manner as in Preparation Example 1, except that 1-butanol was used as the initiator, instead of glycerin.

Preparation Example 7: Preparation of Polymer B2

A polymer B2 was prepared in the same manner as in Preparation Example 2,

TABLE 1

| Polymer | Number of hydroxy groups per molecule | Hydroxy value [mgKOH/g] | Mn (GPC) | Mw/Mn (GPC) | Degree of unsaturation [meq/g] | Content of EO units [mass %] |
|---|---|---|---|---|---|---|
| A1 | 3 | 6.9 | 9090 | 1.10 | 0.005 | 0 |
| A2 | 3 | 17.6 | 8470 | 1.19 | 0.013 | 20 |
| A3 | 3 | 16.4 | 14300 | 1.05 | 0.003 | 80 |
| A4 | 2 | 10.7 | 9990 | 1.06 | 0.006 | 0 |
| A5 | 2 | 11.8 | 9510 | 1.06 | 0.011 | 20 |
| B1 | 1 | 5.5 | 11190 | 1.08 | 0.006 | 0 |
| B2 | 1 | 5.2 | 11430 | 1.08 | 0.005 | 20 |

<Hydroxy Value>

The hydroxy value of the oxyalkylene polymer A is calculated in accordance with the titration method stipulated in JIS K0070: 1992 "Test methods for acid value, saponification value, ester value, iodine value, hydroxyl value and unsaponifiable matter of chemical products".

<Production of Hydroxy Group-Terminated Polyurethane Prepolymer>

Production Example 1

As shown in Table 2, 30 parts by mass of the polymer A1, 70 parts by mass of the polymer A4 and 100 parts by mass in total of toluene and ethyl acetate were added in a reaction container provided with a thermometer, a stirrer and a condenser tube. Then, 0.03 part by mass of a urethane-forming catalyst (dibutyltin dilaurate, manufactured by Tokyo Chemical Industry Co., Ltd.) was added thereto and mixed at 40° C., and 1.51 parts by mass of hexamethylene diisocyanate (Duranate 50M, manufactured by Asahi Kasei Corporation, referred to as "HDI" in Table 1) as the diisocyanate compound was added and reacted at 80° C. The isocyanate index was 80. Heat generation occurred by the reaction, the internal temperature became about 80° C., and the viscosity increased with time. While the mixture was appropriately diluted with ethyl acetate, the mixture was maintained at 80° C. and reacted for 7 hours to obtain a hydroxy group-terminated polyurethane prepolymer (referred to also as "polyurethane prepolymer U1") having an average number of hydroxy groups of 2.3 as a uniform transparent liquid.

Production Example 2

A hydroxy group-terminated polyurethane prepolymer having an average number of hydroxy groups of 2.1 (referred to also as "polyurethane prepolymer U2") was produced in the same manner as in Production Example 1, except that 30 parts by mass of the polymer A2, 40 parts by mass of the polymer A5 and 30 parts by mass of the polymer B1 were used, instead of the polymer A1 and the polymer A4, and 5.00 parts by mass of D201 (isocyanate group-terminated polyurethane prepolymer, manufactured by Asahi Kasei Corporation) was used as the diisocyanate compound, as shown in Table 2.

Production Example 3

A hydroxy group-terminated polyurethane prepolymer having an average number of hydroxy groups of 2.0 (referred to also as "polyurethane prepolymer U3") was produced in the same manner as in Production Example 2, except that 30 parts by mass of the polymer B2 was used, instead of the polymer B1, and 4.91 parts by mass of D201 was used as the diisocyanate compound, as shown in Table 2.

Production Example 4

A hydroxy group-terminated polyurethane prepolymer having an average number of hydroxy groups of 1.9 (referred to also as "polyurethane prepolymer U4") was produced in the same manner as in Production Example 3, except that 30 parts by mass of the polymer A3 was used, instead of the polymer A2, and 4.77 parts by mass of D201 was used as the diisocyanate compound, as shown in Table 2.

<Production of Pressure-Sensitive Adhesive>

[Ex. 1]

As shown in Table 3, 100 parts by mass of the polyurethane prepolymer U1 and 2 parts by mass of a curing agent (Coronate L, tradename of Tosoh Corporation) were uniformly mixed and deaerated, and the mixture was applied on a polyester film to which release treatment was applied (release body, thickness of 50 μm) by means of a knife coater so that the dry film thickness would be 25 μm and dry-cured at 100° C. for 3 minutes. A polyester film (supporting body) having a thickness of 38 μm was bonded on the obtained pressure-sensitive adhesive layer and stored in a hot air dryer under an atmosphere of 50° C. for 3 days to complete the crosslinking reaction of the pressure-sensitive adhesive layer, whereby a pressure-sensitive adhesive was prepared.

The content of ethylene oxide units in the obtained pressure-sensitive adhesive was 0 mass %.

[Ex. 2]

A pressure-sensitive adhesive was produced in the same manner as in Ex. 1, except that the polyurethane prepolymer U2 was used, instead of the polyurethane prepolymer U1, as shown in Table 3. The content of ethylene oxide units in the obtained pressure-sensitive adhesive was 14 mass %.

[Ex. 3]

A pressure-sensitive adhesive was produced in the same manner as in Ex. 1, except that the polyurethane prepolymer U3 was used as the hydroxy group-terminated polyurethane prepolymer, as shown in Table 3. The content of ethylene oxide in the obtained pressure-sensitive adhesive was 20 mass %.

[Ex. 4]

A pressure-sensitive adhesive was produced in the same manner as in Ex. 1, except that the polyurethane prepolymer U4 was used as the hydroxy group-terminated polyurethane prepolymer, as shown in Table 3. The content of ethylene oxide units in the obtained pressure-sensitive adhesive was 38 mass %.

[Ex. 5]

A pressure-sensitive adhesive was produced in the same manner as in Ex. 3, except that 4 parts by mass of Duranate E-402-80B (tradename of Asahi Kasei Corporation) was used as the curing agent, instead of Coronate L, as shown in Table 3. The content of ethylene oxide units in the obtained pressure-sensitive adhesive was 20 mass %.

TABLE 2

| | | | Production Example | | | |
|---|---|---|---|---|---|---|
| | | | 1 | 2 | 3 | 4 |
| Added amount [parts by mass] | Polymer | A1 | 30 | — | — | — |
| | | A2 | — | 30 | 30 | — |
| | | A3 | — | — | — | 30 |
| | | A4 | 70 | — | — | — |
| | | A5 | — | 40 | 40 | 40 |
| | | B1 | — | 30 | — | — |
| | | B2 | — | — | 30 | 30 |
| | Diisocyanate compound | HDI | 1.51 | — | — | — |
| | | D2O1 | — | 5.00 | 4.91 | 4.77 |
| | Catalyst | Dibutyltin dilaurate | 0.03 | 0.03 | 0.03 | 0.03 |
| Average number of hydroxy groups | | | 2.3 | 2.1 | 2.0 | 1.9 |
| Isocyanate index | | | 80 | 90 | 90 | 90 |
| Content of EO units [mass %] | | | 0 | 14 | 20 | 38 |
| Polyurethane prepolymer | | | U1 | U2 | U3 | U4 |

TABLE 3

| | | | Ex. 1 | Ex. 2 | Ex. 3 | Ex. 4 | Ex. 5 |
|---|---|---|---|---|---|---|---|
| Added amount [parts by mass] | Polyurethane prepolymer | U1 | 100 | — | — | — | — |
| | | U2 | — | 100 | — | — | — |
| | | U3 | — | — | 100 | — | 100 |
| | | U4 | — | — | — | 100 | — |
| | Curing agent | Coronate L | 2 | 2 | 1.5 | 1.5 | — |
| | | Duranate E402-80B | — | — | — | — | 4 |
| Content of EO units [mass %] | | | 0 | 14 | 20 | 38 | 20 |
| Properties of pressure-sensitive adhesive | Moisture permeability | [g/m$^3$ · day] | 2,900 | 4,900 | 4,900 | 4,900 | 4,400 |
| | | Evaluation | D | B | B | B | B |
| | Adhesion | To phenol resin [N/15 mm] | 4.8 | 3.4 | 4.3 | 3.5 | 5.0 |
| | | Evaluation | A | A | A | A | A |
| | | To skin [N/15 mm] | 0.02 | 0.5 | 0.5 | 0.4 | 0.4 |
| | | Evaluation | D | A | A | A | A |
| | Difference in adhesion | [N/15 mm] | 4.8 | 2.9 | 3.8 | 3.1 | 4.6 |
| | | Evaluation | A | A | A | A | A |
| | Storage elastic modulus | 25° C. [Pa] | 4.1 × 10$^5$ | 3.1 × 10$^5$ | 3.0 × 10$^4$ | 4.6 × 10$^5$ | 3.1 × 10$^4$ |
| | | 80° C. | 2.8 × 10$^5$ | 1.3 × 10$^5$ | 6.3 × 10$^3$ | 1.6 × 10$^5$ | 2.5 × 10$^3$ |

In Table 2, the added amounts of the polymer, the diisocyanate compound and the catalyst are represented by parts by mass. Further, "isocyanate index" is a value obtained by dividing the number of moles of isocyanate groups in the diisocyanate compound used for producing the hydroxy group-terminated polyurethane prepolymer by the total number of moles of hydroxy groups in the oxyalkylene polymers and multiplying the quotient by 100, and "content of EO units" is the mass ratio (unit: mass %) of ethylene oxide units in the hydroxy group-terminated polyurethane prepolymer. "–" means that the component is not contained.

In Table 3, the added amounts of the polyurethane prepolymer and the curing agent are represented by parts by mass. "Content of EO units" is the proportion (unit: mass %) of ethylene oxide units in the pressure-sensitive adhesive. "–" means that the component is not contained.

[Evaluations of Properties of Pressure-Sensitive Adhesive]

The moisture permeability, the adhesion to a phenol resin, the adhesion to the human skin, the difference between the adhesion to a phenol resin and the adhesion to the human skin and the storage elastic modulus of the pressure-sensitive adhesives in Ex. 1 to 5 were evaluated. Results are shown in Table 3. Unless otherwise specified, test specimens were produced by cutting the adhesive skin patches to be 15 mm in width×60 mm in length so that the machine direction of originally wound adhesive skin patches would be the long side direction (MD direction). Further, the supporting body and the release body were released from the adhesive skin patch for the measurement.

<Moisture Permeability>

The moisture permeability was obtained as the mass of water vapor which passes through the test specimen per 1 m$^2$ in 24 hours (1 day).

100 parts by mass of the produced polyurethane prepolymer and a curing agent (Coronate L (tradename of Tosoh Corporation) or Duranate E402-80B (tradename of Asahi Kasei Corporation)) in the amount shown in Table 3 were uniformly mixed and deaerated, and applied on a polyester film to which release treatment was applied (release body, thickness of 50 μm) by means of a knife coater so that the dry film thickness would be 25 μm and dry-cured at 100° C. for 3 minutes to form a pressure-sensitive adhesive layer on the release body. A rough nylon net which had no influence over the moisture permeability of the pressure-sensitive adhesive was attached to the obtained pressure-sensitive adhesive layer, and stored in a hot air dryer under an atmosphere of 50° C. for 3 days to complete the crosslinking reaction of the pressure-sensitive adhesive layer, and the release body was released to prepare a test specimen.

As the measurement of the moisture permeability, under an atmosphere of 40° C., the relative humidity of one side space separated by the test specimen was set to 90%, the other side space was kept in a dry state by a moisture absorbent, and the mass (g) of water vapor which passed through the test specimen in 24 hours (one day) was measured and converted to a value per 1 m$^2$ of the test material. The measurement was carried out in accordance with JIS Z0208: 1976 "Testing methods for Determination of the Water Vapor Transmission Rate of Moisture-Proof Packaging Materials (Dish Method)". A cup containing about 50 g of a calcium chloride moisture absorbent was covered with a disk shape test specimen having a diameter larger by about 10 mm than the inner diameter of the cup, the test specimen was fixed by a rubber packing and a ring, and the cup was screwed up. The total mass of the test specimen was measured, and the cup is put in a thermo-hygrostat at 40° C. under a 90% RH atmosphere, the change of the mass was measured at constant intervals, and the moisture permeability was measured in accordance with the following formula.

Moisture permeability(g/m$^2$·day)=W×240,000/S wherein S is a moisture permeation area (cm$^2$), and W is a mass increase per hour (g/hr).

The moisture permeability was evaluated based on the following standard.

A: at least 5,000 g/m$^2$·day
B: at least 4,000 g/m$^2$·day and less than 5,000 g/m$^2$·day
C: at least 3,000 g/m$^2$·day and less than 4,000 g/m$^2$·day
D: less than 3,000 g/m$^2$·day The calculated moisture permeability and evaluation results of the moisture permeability are shown in the row of "Moisture permeability" in Table 3.

<Adhesion to Phenol Resin>

The peel strength was measured in accordance with the test method stipulated in JIS Z0237: 2009 "Test methods of pressure-sensitive adhesive tapes and sheets, 10 Adhesion", as follows. A test specimen having a width of 15 mm was attached to a Bakelite panel (phenolic resin board, manufactured by Sumitomo Bakelite Co., Ltd., PL-1102) under an atmosphere of 25° C., pressure-bonded by reciprocating a 2 kg rubber roll once at a rate of 300 mm/min and left to stand for 20 minutes, and the peel strength at a peel angle of 90° or 180° at a peel rate of 300 mm/min was measured.

The adhesion to a phenol resin was evaluated based on the following evaluation standard.

A: at least 3.0 N/15 mm
B: at least 2.5 N/15 mm and less than 3.0 N/15 mm
C: at least 2.0 N/15 mm and less than 2.5 N/15 mm
D: less than 2.0 N/15 mm The measured adhesion to a phenol resin and evaluation results of the adhesion to a phenol resin are shown in the row of "Adhesion to phenol resin" in Table 3.

<Adhesion to Human Skin>

The measurement was carried out in the same manner as in the adhesion to a phenol resin, except that the back of a human hand was used, instead of the bakelite panel. The back of a human hand was degreased with isopropyl alcohol and air-dried for use.

The adhesion to the human skin was evaluated based on the following standard.

A: from 0.2 to 1.0 N/15 mm
D: less than 0.2 N/15 mm or higher than 1.0 N/15 mm

The measured adhesion to the human skin and evaluation results of the adhesion to the human skin are shown in the row of "adhesion to skin" in Table 3.

<Difference Between Adhesion to Phenol Resin and Adhesion to Human Skin>

The difference between the adhesion to a phenol resin and the adhesion to the human skin was calculated by the following formula.

"Difference between adhesion to phenol resin and adhesion to the human skin"="adhesion to phenol resin"–"adhesion to human skin"

The difference between the adhesion to phenol and the adhesion to human skin was evaluated based on the following standard.

A: at least 2.5 N/15 mm
B: at least 2.0 N/15 mm and less than 2.5 N/15 mm
C: at least 1.5 N/15 mm and less than 2.0 N/15 mm
D: less than 1.5 N/15 mm The calculated difference between the adhesion to a phenol resin and the adhesion to the human skin and evaluation results of the difference between the adhesion to phenol and the adhesion to the human skin are shown in the row of "difference in adhesion" in Table 3.

<Storage Elastic Modulus>

100 parts by mass of the produced polyurethane prepolymer and a curing agent (Coronate L (tradename of Tosoh Corporation) or Duranate E402-80B (tradename of Asahi Kasei Corporation)) in the amount shown in Table 3 were uniformly mixed and deaerated, and applied on a polyester film to which release treatment was applied (release body, thickness of 50 μm) by means of a knife coater so that the dry film thickness would be 25 μm and dry-cured at 100° C. for 3 minutes to form a pressure-sensitive adhesive layer on the release body. A release body was attached to the obtained pressure-sensitive adhesive layer, and stored in a hot air dryer under an atmosphere of 50° C. for 3 days to complete the crosslinking reaction of the pressure-sensitive adhesive layer. The release body was peeled, and the adhesive tape was cut into a size of 4 cm in width and 30 cm in length, and wound into a cylinder having a diameter of about 3 mm and a length of 4 cm to prepare a test sample. The storage elastic modulus E' is a value obtained by measuring a storage elastic modulus E' (kPa) under a condition of strain of the obtained test sample of 1% under the following measuring conditions. The storage elastic moduli at 25° C. and at 80° C. are shown in Table 3.

Measuring device: dynamic viscoelasticity measuring device (EXSTAR 6000 DMS 6100, manufactured by Seiko Instruments Inc.)
Mode: tensile mode
Temperature: −80 to 130° C.
Rate of temperature increase: 3° C./min
Measuring frequency: 1 Hz

[Explanation of Results]

In Table 3, Ex. 2 to 5 correspond to Examples of the present invention, and Ex. 1 corresponds to a Comparative Example of the present invention.

When the evaluation of the moisture permeability is A, B or C, the pressure-sensitive adhesive is excellent in the moisture permeability.

When the evaluation of the adhesion to a phenol resin is A, B or C, the evaluation of the adhesion to the skin is A, and the evaluation of the difference in the adhesion is A, B or C, both low adhesion to the skin and high adhesion to a substrate can be established.

Accordingly, the pressure-sensitive adhesives in Ex. 2 to 5 are excellent in the moisture permeability and have both low adhesion to the skin and high adhesion to a substrate. On the other hand, the pressure-sensitive adhesive in Ex. 1 has a low moisture permeability and a too low adhesion to the skin. The reason is considered that the content of EO units is low, and the polarity of the pressure-sensitive adhesive is low.

INDUSTRIAL APPLICABILITY

The pressure-sensitive adhesive using the polyurethane prepolymer of the present invention has an excellent moisture permeability, and has a low adhesion to the skin and a high adhesion to a substrate, whereby the pressure-sensitive adhesive is particularly preferably used as a pressure-sensitive adhesive for attaching various wearable devices.

This application is a continuation of PCT Application No. PCT/JP2020/006116, filed on Feb. 17, 2020, which is based upon and claims the benefit of priority from Japanese Patent Application No. 2019-036306 filed on Feb. 28, 2019. The contents of those applications are incorporated herein by reference in their entireties.

What is claimed is:

1. A pressure-sensitive adhesive, obtained by a process comprising:
reacting an oxyalkylene polymer A having an average number of hydroxy groups per molecule of from 2.1 to 3, an oxyalkylene polymer B having one hydroxy group per molecule, and a polyisocyanate compound, wherein
the pressure-sensitive adhesive has a difference between adhesion to a phenol resin and adhesion to human skin of at least 2 N/15 mm,
the oxyalkylene polymer B has a number average molecular weight of at least 5,000,
the oxyalkylene polymer B has a molecular weight distribution Mw/Mn of less than 1.20 where Mw is a mass average molecular weight and Mn is a number average molecular weight,
the oxyalkylene polymer B has a degree of unsaturation of at most 0.015 meq/g, and
the pressure-sensitive adhesive has a content of ethylene oxide units of at least 10 mass %.

2. The pressure-sensitive adhesive of claim 1, wherein the number average molecular weight of the oxyalkylene polymer B is more than 5,000.

3. The pressure-sensitive adhesive of claim 1, wherein the oxyalkylene polymer A includes an oxyalkylene polymer a having three hydroxy groups per molecule and an oxyalkylene polymer b having two hydroxy groups per molecule.

4. The pressure-sensitive adhesive of claim 3, wherein the content of ethylene oxide units in the oxyalkylene polymer a is at least 15 mass %.

5. The pressure-sensitive adhesive of claim 1, wherein the content of ethylene oxide units in the pressure-sensitive adhesive is from 12 to 50 mass %.

6. The pressure-sensitive adhesive of claim 1, wherein the pressure-sensitive adhesive has a storage elastic modulus at 80° C. of at most $4.0 \times 10^5$ Pa.

7. The pressure-sensitive adhesive of claim 1, wherein the pressure-sensitive adhesive has a moisture permeability of at least 3,000 g/m$^2$·day.

8. The pressure-sensitive adhesive of claim 1, wherein the pressure-sensitive adhesive has an adhesion to human skin, of from 0.2 to 1 N/15 mm.

9. An adhesive skin patch, comprising:
a substrate; and
a pressure-sensitive adhesive layer formed on a surface of the substrate and comprising the pressure-sensitive adhesive of claim 1.

10. A pressure-sensitive adhesive tape, comprising:
a substrate; and
a pressure-sensitive adhesive layer formed on at least one surface of the substrate and comprising the pressure-sensitive adhesive of claim 1.

11. A wearable device, comprising:
a wearable device body; and
a pressure-sensitive adhesive layer formed on at least a part of an adherend surface of the wearable device body and comprising the pressure-sensitive adhesive of claim 1.

12. A wearable device kit, comprising:
a wearable device body; and
the pressure-sensitive adhesive of claim 1 for attaching the wearable device body to skin.

13. A wearable device kit, comprising:
a wearable device body; and
the adhesive skin patch of claim 9 for attaching the wearable device body to skin.

14. A wearable device kit, comprising:
a wearable device body; and
the pressure-sensitive adhesive tape of claim 10 for attaching the wearable device body to skin.

15. The pressure-sensitive adhesive of claim 2, wherein the oxyalkylene polymer A includes an oxyalkylene polymer a having three hydroxy groups per molecule and an oxyalkylene polymer b having two hydroxy groups per molecule.

16. The pressure-sensitive adhesive of claim 15, wherein the content of ethylene oxide units in the oxyalkylene polymer a is at least 15 mass %.

17. The pressure-sensitive adhesive of claim 2, wherein the content of ethylene oxide units in the pressure-sensitive adhesive is from 12 to 50 mass %.

18. The pressure-sensitive adhesive of claim 2, wherein the pressure-sensitive adhesive has a storage elastic modulus at 80° C. of at most $4.0 \times 10^5$ Pa.

19. The pressure-sensitive adhesive of claim 2, wherein the pressure-sensitive adhesive has a moisture permeability of at least 3,000 g/m$^2$·day.

20. The pressure-sensitive adhesive of claim 2, wherein the pressure-sensitive adhesive has an adhesion to human skin, of from 0.2 to 1 N/15 mm.

21. The pressure-sensitive adhesive of claim 3, wherein the content of ethylene oxide units in the pressure-sensitive adhesive is from 12 to 50 mass %.

22. The pressure-sensitive adhesive of claim 3, wherein the pressure-sensitive adhesive has a storage elastic modulus at 80° C. of at most $4.0 \times 10^5$ Pa.

23. The pressure-sensitive adhesive of claim 1, wherein the oxyalkylene polymer B has an ethylene oxide content of 5 to 80%.

* * * * *